United States Patent [19]

Warzeka

[11] Patent Number: 4,898,165

[45] Date of Patent: Feb. 6, 1990

[54] BREATHING APPARATUS

[76] Inventor: Lyle Warzeka, 2064 11th St., Wyandotte, Mich. 48192

[21] Appl. No.: 281,847

[22] Filed: Dec. 8, 1988

[51] Int. Cl.[4] .............................................. A61M 15/00
[52] U.S. Cl. .............................. 128/204.18; 137/512.3; 137/496; 128/205.24; 128/205.12
[58] Field of Search ...................... 128/204.18, 204.28, 128/204.29, 205.24, 205.25, 205.12, 205.13, 205.14, 205.15, 205.27, 206.16, 206.17; 137/526, 512.3, 496

[56] References Cited

U.S. PATENT DOCUMENTS

| | | | |
|---|---|---|---|
| 1,506,584 | 8/1924 | Homan | 128/202.16 |
| 2,847,001 | 8/1958 | Andreasen | 128/205.24 |
| 2,948,292 | 8/1960 | Fitt | 128/204.29 |
| 3,556,122 | 1/1971 | Laerdal | 137/512.3 |
| 4,180,066 | 12/1979 | Milliken et al. | 128/204.18 |
| 4,446,863 | 5/1984 | Rubin et al. | 128/204.18 |
| 4,782,831 | 11/1988 | Gallant | 128/204.18 |
| 4,794,922 | 1/1989 | Devries | 128/204.18 |

FOREIGN PATENT DOCUMENTS 865830 4/1961 United Kingdom .................. 204/29

OTHER PUBLICATIONS

Understanding Anesthesia Equipment, Jerry A. Dorsch, Susan R. Dorsch, Chapter 7, "The Breathing System", Williams & Williams, 1984, Baltimore, Md., pp. 203-204.

Primary Examiner—Eugene H. Eickholt
Attorney, Agent, or Firm—Dykema Gossett

[57] ABSTRACT

A universal manual resuscitator vavle which includes a filter is provided by which breathing circuit system elements can be protected from contamination by contaminants present in exhalation gases. In one embodiment, the valve assembly includes a valve flap which is attached at opposite edges and which is resiliently urged into a position such that an exhalation stack is closed in mode of operation.

10 Claims, 3 Drawing Sheets

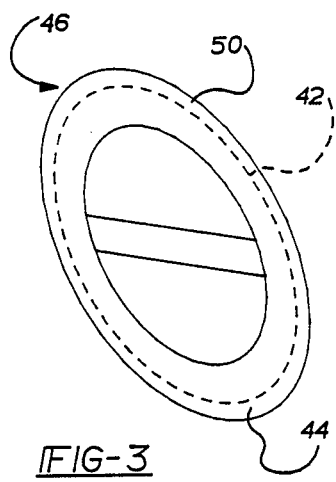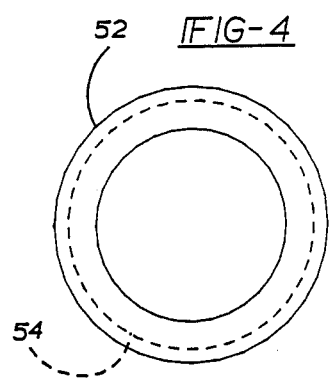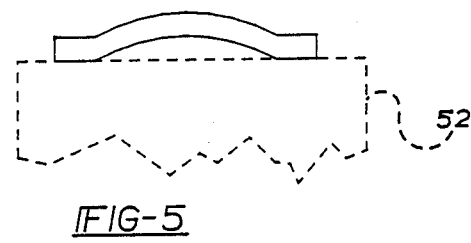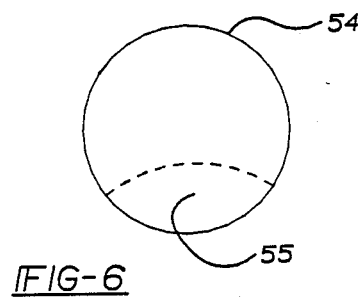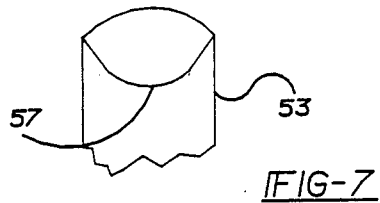

4,898,165

BREATHING APPARATUS

FIELD OF THE INVENTION

The present invention relates to various breathing apparatus which are used in connection with breathing systems to administer air or other gases to a patient. More specifically, the present invention relates to a breathing apparatus which solves numerous problems inherent in conventional breathing devices.

BACKGROUND OF THE INVENTION

Various breathing systems have been developed to provide means by which air or other gases can be administered to a patient from a gas source such as a compressed gas container or directly from the atmosphere. For example, it is often necessary during the treatment of a patient to administer an anesthetic mixture of gases from an anesthesia machine. Moreover, it is sometimes necessary to administer pulmonary resuscitation to a patient following surgery or when voluntary breathing has been interrupted due to an illness or injury.

As known by those skilled in human physiology, respiration involves the exchange of gases in the lungs. Breathing can be described as the mechanical process by which air is drawn into and expelled from the lungs by muscular contractions in the rib cage and diaphragm. Inhalation is an active process whereby the thoracic volume is increased through muscle contraction. Exhalation is a passive process wherein the contracted muscles relax, causing the thoracic volume to be reduced. This reduction in lung volume raises the air pressure inside the lungs such that air in the lungs is expelled through the airways into the atmosphere.

One problem inherent in the exhalation of air from the lungs which has received considerable attention recently due to an increased knowledge of infectious processes and due to the discovery of new, highly contagious viruses, is crosscontamination caused by the expiration of an infectious organism. More specifically, it is known that exhalation often produces an aerosol of tiny water droplets in which an infectious agent may reside. It is also known that viruses such as influenza and like are commonly transferred from one individual to another, a process referred to as cross-infection, as the direct result of the exhalation of infectious aerosol. In essence, the infectious agent is able to survive outside of the body in these tiny water droplets. Moreover, these droplets may deposit on a substratum where they remain biologically active for some time. This latter phenomenon may lead to cross infection due to surface contamination. In my U.S. patent application Ser. No. 026,067, filed Mar. 16, 1987, I disclose novel breathing systems which utilize integral bacterial/viral filters that prevent contamination of breathing systems to reduce the possibility of cross-infection. The present invention, as will be explained more fully below, provides yet another novel solution to the problem of contamination of breathing systems by exhalation or expiration of infectious agents which is a significant problem with most conventional breathing apparatus.

In particular, there are a number of prior art breathing valve assemblies which may be used with a manual resuscitation bag or the like. One such valve assembly includes a complicated set of springs, balls and valve seats which responds to air pressure differentials in the breathing system to open and close air passages. These devices are not only expensive to manufacture, but the ball valves are particularly sensitive to gravitational forces rendering the valve assembly position sensitive. Thus, the patient must be precisely positioned to accommodate the position sensitivity of the valve. In addition, these prior art breathing valve assemblies generally provide substantial resistance to air flow, making it difficult to compress the resuscitation bag during operation. As those skilled in the art will appreciate, ease of bag compression is a highly desirable attribute of manual resuscitators.

Also, it is also known that many conventional manual resuscitation systems require an intake valve on the bag in order that the resuscitator bag may be refilled with air or air/oxygen.

The present invention solves these prior art problems in a manner in which transmission of pathogens from the patient's aerosol to the resuscitation bag can be reduced or eliminated, thus making the resuscitator bag reusable and reducing resuscitator costs to hospitals.

BRIEF DESCRIPTION OF THE DRAWINGS

FIG. 3 is an end view of one portion of the device in the direction of arrow A in FIG. 2.

FIG. 4 is a view of a portion of the device shown in FIG. 2 in the direction of arrow B in FIG. 1.

FIG. 5 is a plan view of the flap shown in phantom in FIG. 4.

FIG. 6 is a side elevational view of the flap shown in FIG. 5.

FIG. 7 is a perspective view of one stack of the present invention.

SUMMARY OF THE INVENTION

In accordance with the present invention, a universal manual resuscitator valve is provided which includes a valve body having a bore therethrough which defines a gas passage. Attached to the valve body and extending partially into the bore is an annular valve seat. A valve element, preferably a valve flap, is attached to one portion of the valve body and is positioned in the bore adjacent the annular valve seat.

In one mode of operation, the valve flap seats on the annular valve seat to that the valve body passage is partitioned into a first portion and a second portion. Leading into the first portion of the passage the valve body includes an exhalation stem or tube which has a first end projecting outwardly from the valve body and a second end which projects into the valve body bore at the first portion of the passage. This internal or first end of the exhalation tube is beveled or angled. The beveled end is positioned with respect to the valve flap such that in another mode the flap seats on the beveled end closing the exhalation tube. The valve body further includes an inlet port which leads into the second portion of the passage. The inlet port includes a second valve. The second valve includes a recessed portion which prevents a complete or air-tight seal of the inlet port to prevent lock-up during patient exhalation.

In operation, the universal manual resuscitator valve is used in connection with a disposable face mask which is attached to the valve body in association with the first portion of the passage. A viral bacterial filter is preferably attached to the valve body. A reusable resuscitator bag is attached to the filter in association with the second portion of the passage. A source of fresh gases is preferably attached to the inlet port. During operation, fresh gases flow through the valve at the inlet port, which is open, through the filter and into the resuscitator bag. Once the bag is sufficiently filled with fresh gases the bag is compressed. The gas pressure for the resuscitation bag closes the inlet port valve and forces the other valve flap into the mode where it closes the exhalation tube. Fresh gases continue through the passage downwardly into the face mask and into the patient's lungs. During patient exhalation, the exhalation gas pressure moves the valve flap from its position on the beveled end of the exhaust tube onto the annular valve seat such that exhalation gases must move out through the exhalation tube from the first portion of the passage. In this manner, exhalation gases are prevented from entering the second portion of the passage, whereby contamination of the resuscitator bag is prevented. The recessed portion of the flap prevents lock-up of the valve flap on the exhaust tube.

DESCRIPTION OF THE PREFERRED EMBODIMENTS

Figure 1:
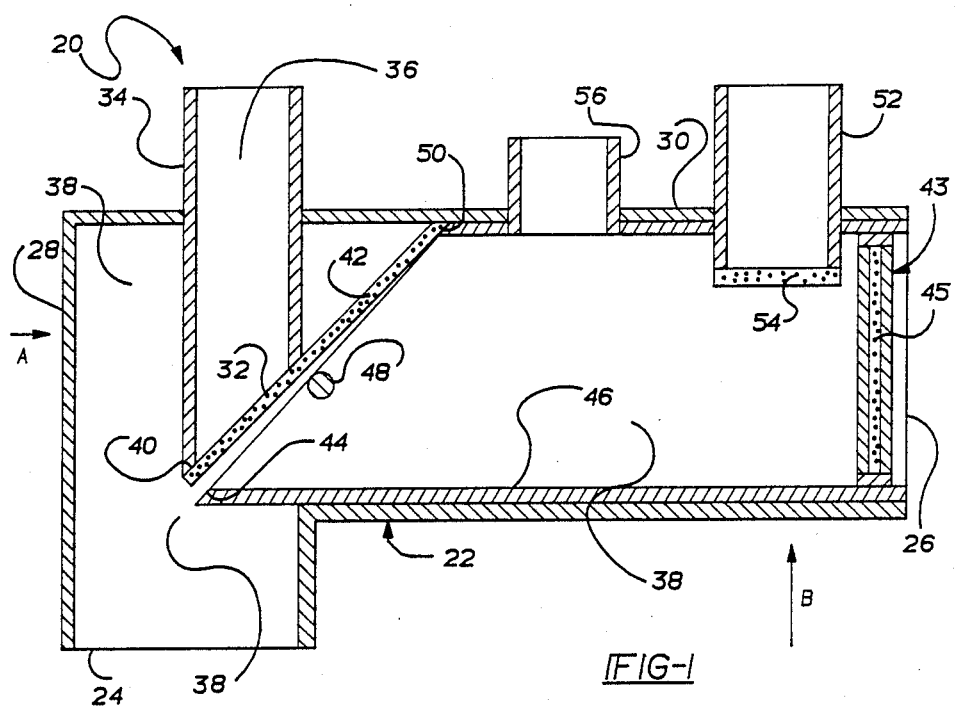
FIG. 1 is a longitudinal cross-section of one embodiment of the present invention in one mode of operation during patient inhalation when the resuscitation bag is being squeezed.

Referring now to FIG. 1 of the drawings, universal manual resuscitator valve 20 is provided, shown generally having universal manual resuscitator valve body 22 with mask connection portion 24 and resuscitator bag connection portion 26. In this embodiment, universal manual resuscitator valve body 22 has an L-shaped configuration. For the purposes of this description, universal manual resuscitator valve body 22 may be considered as having a vertical portion 28 and a horizontal portion 30. At horizontal portion 30 there is provided exhalation or exhaust port 32 and exhalation stem 34 which defines exhalation passage 36. As shown, exhalation stem 34 extends into gas passage 38 of valve body 22. It is to be understood that passage 38 extends throughout valve body 22. Beveled or angled end 40 of exhalation stem 34 serves as a valve seat for valve flap 42.

A second valve seat 44 for valve flap 42 is also provided which comprises an annular rim or shoulder defined by internal casing 46 and which extends into the bore of vertical portion 28 of valve body 22. A stop in the form of transverse bar 48 which spans the opening defined by valve seat 44 is provided to prevent valve flap 42 from being sucked past valve seat 44 toward bag connection portion 26 upon bag refill. Valve seat 44 is also at an angle as shown in FIG. 1. Valve flap 42 is connected to valve seat 44 at attachment site 50. When mask connection portion 24 is connected to a breathing face mask and the mask is in place on a patient's face, flapper valve 42 abuts lightly on valve seat 44. It is preferred that the angle of valve seat 44 be at approximately 45 degrees with respect to horizontal portion 30. This is true also for beveled end 40 as shown in FIG. 1.

Near bag connection portion 26 of horizontal portion 30 there is provided air or gas inlet port 52. Air inlet port 52 is also provided with a valve flap 54, the function of which will be more fully explained hereinafter. Valve flap 42 and 54 may be made of numerous materials such as rubber or resilient plastic so long as their movement and resiliency are consistent with the function of the present invention. Other than valve flaps or members 42 and 54, all of the components are rigidly connected to one another. It is preferred that valve flap or member 42 be flexible enough such that it deforms somewhat when closing exhalation passage 36 to allow maximum air flow through passage 38. It is to be understood that passage 38 is defined by valve body 22 and is the passage through which air or the like flows from bag connection portion 26 to mask end 24. Valve flap 42 is shown in FIG. 1 seated on beveled end 40 in that mode in which valve flap 42 closes exhalation passage 36. Also, it is preferred that universal manual resuscitator valve include manometer pressure gauge port 56 by which gas pressure inside air passage 38 can be monitored. Filter 43 having filter media 45 is also provided. Filter media 45 preferably blocks contaminants such as bacteria and viruses which may be present.

In operation, a reusable resuscitator bag (not shown) is connected to portion 20 and compressed whereupon valve flap 54 closes air intake stack 52 in response to the flow of air from the resuscitator bag. Air from the bag flows through filter 43 and filter media 45. Air flow continues along air passage 38 toward valve flap 42, moving valve flap 42 into the closed position as shown in FIG. 1. That is, valve flap 42 seats on beveled end 40 of exhalation stem 34 closing exhalation passage 36. With the exhalation passage 36 now closed, air continues along passage 38 into the face mask whereby the patient's lungs are ventilated.

Figure 2:
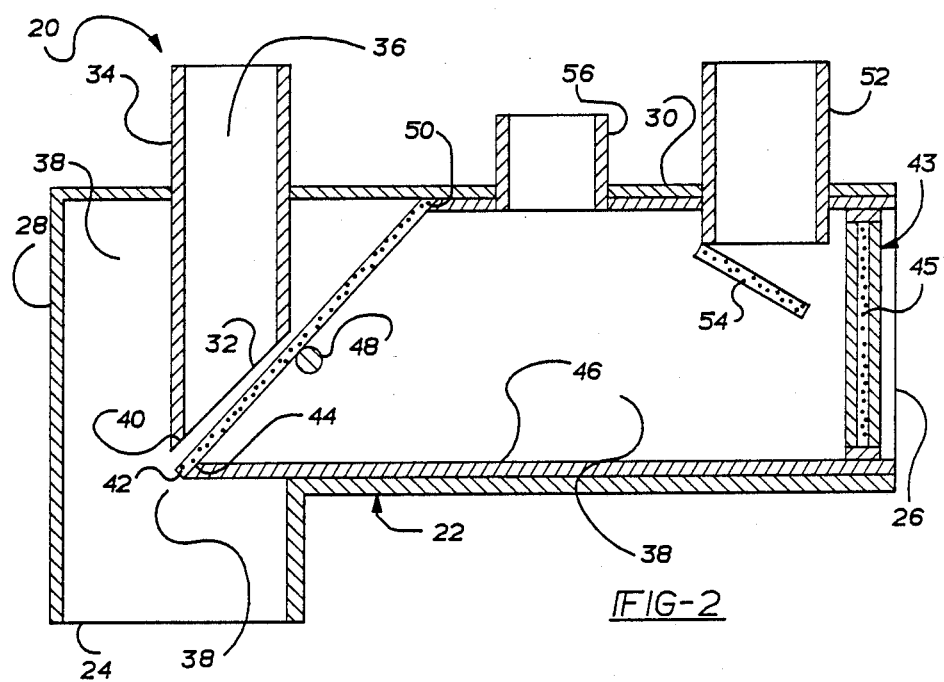
FIG. 2 is a longitudinal cross-section of the device illustrated in FIG. 1 in a second mode of operation during patient exhalation when the resuscitation bag is being inflated.

During exhalation, the resuscitator bag is decompressed and, as the patient exhales, exhalation gases travel through passage 38 in the opposite direction of fresh gas flow forcing valve flap 42 to move against valve seat 44 as best shown in FIG. 2. In this position, the horizontal portion of air passage 38 is partitioned such that the exhalation gases must flow through exhalation passage 36 of exhalation port 32. Any aerosol which could possibly contaminate the bag is effectively stopped by filter 43 by virtue of filter element 45. Of course, the filter 43 similarly filters air flowing from the bag to the patient. Filter element 45 can be made of a material well known to those skilled in the art such as a bacterial/viral filter formed of fiberglass, foam or paper with a low-flow resistance which does not substantially impede the flow of air from the bag to the patient. Simultaneously, the decompression of the resuscitation bag creates a vacuum which draws air or oxygen from an oxygen supply in through inlet port 52 by opening valve flap 54 to fill the resuscitation bag. The bore of inlet port 52 should be large enough to permit rapid refilling of the resuscitation bag. The internal diameter of inlet port 52 is preferably greater than 0.5 inches. Preferably, flap 54 should be hinged at that portion of inlet port 52 closest to gauge port 56. In this manner, exhalation gases are prevented from contaminating the resuscitation bag since they are safely vented through exhalation port 32. Port 32 may be connected to a peep valve or the like. Also, it is preferred that universal manual resuscitator valve body 22 be formed of a transparent material so that the valve action can be observed. The flaptype design of this invention provides a valve system having extremely low resistance to air flow. This feature facilitates the use of a filter.

Referring to FIG. 3 of the drawings, the attachment and relative position of flap 42 with respect to internal casing 46 is shown more clearly. FIG. 3 illustrates an end view of casing 46 in the direction of arrow A of FIG. 1. For clarity, the remainder of valve 20 is not shown. Clearly shown in the relationship of valve flap or member 42 which is shown in phantom and valve seat 44 which comprises the end of the tubular internal casing 46. It will be understood by those skilled in the art then that the thickness of the tubular sections which are used to form valve 20 should be thick enough to provide good strength and durability, preferably a thickness of approximately one-sixteenth inch, and where the end of the tube wall serves as a valve seat, the tube should be thick enough to provide adequate area for valve contact. A tube wall thickness of about one-sixteenth inch is sufficient. The tubes may be made from a variety of materials; however, clear or transparent plastic is preferred since it allows the health care administrator to view the operation of the valves. Also, as illustrated in FIG. 3, transverse bar 48 is shown which, again, prevents valve flap 42 from moving into the bore of internal casing 46 during operation, although this is unlikely. At attachment point 50, flap 42 can be connected by any convenient means such as a suitable amount of an adhesive.

In FIG. 4, the relative position of valve flap 54, shown in phantom, and intake stack 52 is illustrated. In this embodiment, the arrangement and attachment of valve flap 54 to intake stack 52 is identical to that used for the attachment of valve flap 42 to internal casing 46 and will not be further explained.

In FIG. 5 of the drawings, an alternate arrangement of valve flap 54 is depicted. At times, valve flap 54 may cause valve flap 42 to "lock-up" onto exhalation stem 34 during patient exhalation. This may occur if flap 54 completely closes stack 52 during exhalation. In order to prevent lock-up from occurring, as a safety measure, and as shown in FIGS. 5 and 6 of the drawings, valve flap 54 may be constructed such that it is slightly concave, at least in that portion designated as region 55. This may be achieved during the molding process or simply by placing a piece of adhesive tape or the like on valve flap 54, expanding the tape by pulling on its end, and then allowing the tape to contract, whereupon a slight bowing effect is achieved. The bowed nature of flap 54 generally prevents a complete or air-tight seal from occurring between flap 54 and stack 52, thus preventing lock-up. In FIG. 7, another arrangement of flap 54 and corresponding stack 52 is shown which prevents lock-up. As illustrated, stack 52 includes a reduced portion 57. Reduced portion 57 allows air to pass by flap 54 during patient exhalation to prevent lock-up. Reduced portion 57 will typically be concave and may be approximately one-half inch wide and 1/64 inch in depth. In other words, stack end 53 is recessed somewhat so that it slopes downwardly. When flap 54 then seats on end 53, the seal is incomplete until the bag is squeezed, whereupon a complete seal is achieved.

Figure 8:
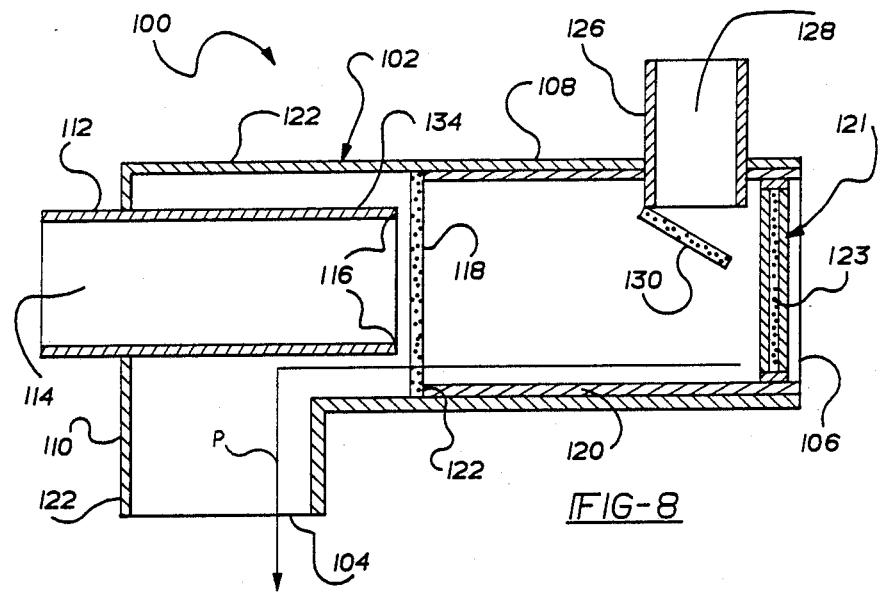
FIG. 8 is a longitudinal cross-section of another embodiment of the present invention in one mode of operation during patient exhalation and when the resuscitation bag is being inflated.
Figure 9:
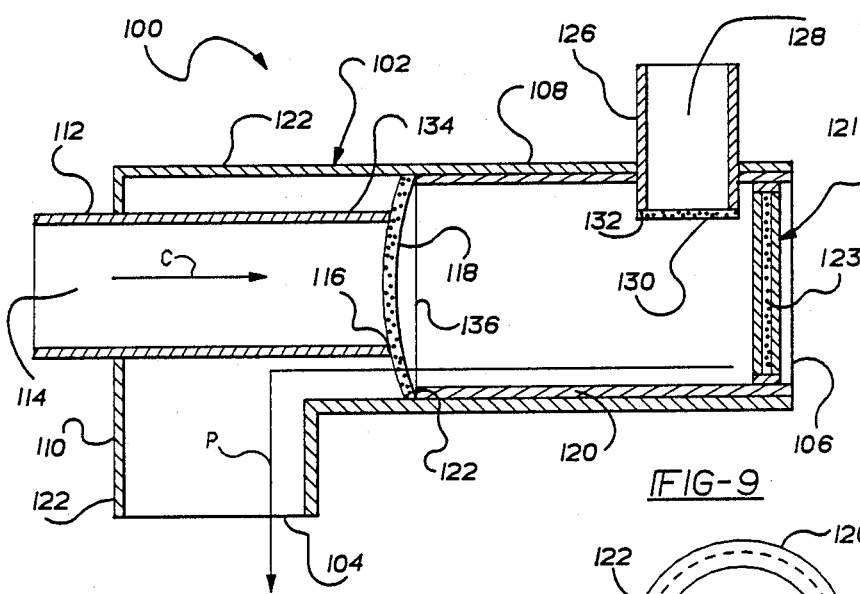
FIG. 9 is a longitudinal cross-section of the device shown in FIG. 8 in another mode of operation during patient inhalation when the resuscitation bag is being squeezed

Referring now to FIGS. 8 and 9 of the drawings, in another embodiment of the present invention, valve assembly 100 is shown generally having valve body 102. Valve assembly 100 carries out the same function as universal valve 20 which was described earlier. Valve body 102 includes mask connection portion 104 and bag connection portion 106 at opposite ends. Valve body 102 is provided in this embodiment with a horizontal portion 108 and a vertical portion 110. It is to be understood, as with the earlier embodiments, that these portions 108 and 110 are defined simply to aid in the description of the invention. At vertical portion 110 of valve body 102, exhalation tube 112 is provided which defines exhalation passage 114. One end of exhalation tube 112 will serve as valve seat 116 for valve flap 118 during operation. Again, internal casing 120 is provided which forms a "tube-in-tube" type arrangement for valve body 102 with respect to outer casing 122 of valve body 102.

Valve flap 118, preferably a latex material of approximately 1.0 ml, is attached preferably at site 122 on the rim or end of internal casing 120. The end of internal casing 120 also serves as a seat at whose surface wherein valve flap 118 is not attached to internal casing 120, as will be explained more fully hereinafter. Again, a filter 121 is provided having a viral/bacterial filter element 123 to filter out viruses and bacteria.

Penetrating both outer casing 122 and inner casing 120, there is seen gas inlet port or stack 126 which defines gas inlet passage 128. The flow of gas through passage 128 is controlled by valve flap 130 which is again attached at site 132 at one end of stack 126 with the end of stack 126 serving as a valve seat for valve flap 130. The materials and other considerations which were explained more fully in connection with the description of FIGS. 1 and 2 of the drawings are applicable here. The relative position of end 134 of tube 114 with respect to valve flap 118 such that flap 118 can be urged by a pressure differential toward end 134, such as by squeezing the bag, to create an air-tight seal for air passage 114 is shown best in FIG. 10 of the drawings.

In FIG. 9, the relative position of flap 118 and internal casing 120 is shown on valve seat 136. Preferably, flap 118 is attached to internal casing 120 at point 122 of valve seat 136. Again, valve seat 136 is simply the end of the tube which comprises internal casing 120. The aforementioned arrangements of flap 54 with respect to inlet stack 52 can be used in this embodiment of the invention for the attachment and positioning of flap 130 with respect to stack 126. Again, the recessed arrangement or bowed flap would be used to prevent lock-up as previously described. A manometer pressure gauge port (not shown) by which gas pressure inside valve body 122 can be monitored can also be provided as previously described.

Figure 10:
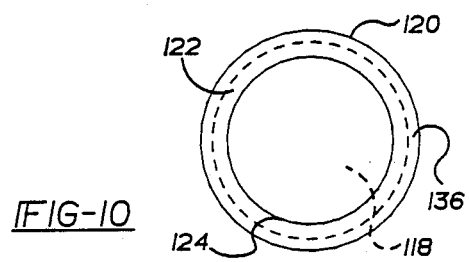
FIG. 10 is a view of a portion of the device shown in FIG. 8 in the direction of arrow C.

In operation, a re-usable resuscitator bag (not shown) is connected to valve assembly 100 at bag connection end 106. A standard face mask or the like is connected to valve assembly 100 at mask connection portion 104. The mask is placed over a patient's face, and the resuscitator bag is compressed whereupon valve flap 130 closes air intake stack 126 or, in other words, closes off air intake passage 128 and responds to the flow of air from the resuscitator bag. Air from the resuscitator bag moves in the direction of arrow P through casing 120 whereupon it encounters flap 118. The differential air pressure moves or urges flap 118 as shown in FIG. 10 of the drawings such that it closes off air passage 114. Flap 118 is sufficiently resilient to move in this manner and, since it is "tacked on" by an adhesive or the like only at point 122 to internal casing 120, air inside the bore of internal casing 120 escapes between flap 118 and valve seat 136. Thus, the exhalation passage 114 is thereby closed off. Air then continues along in the direction of arrow P through valve assembly 100 to the face mask, whereby the patient's lungs are ventilated.

During exhalation, the resuscitator bag is decompressed and, as the patient exhales, exhalation gases travel in the reverse direction from the mask toward flap 118. In response, flap 118 seals off the bore of internal casing 120 such that the exhaust or exhalation gases must flow into end 134 of tubing 112 and out of valve body 122 via exhalation passage 114 where they are vented to the atmosphere. This mode of operation is shown in FIG. 8. Simultaneously, the decompression of the resuscitation bag creates a vacuum which draws air or oxygen from an oxygen supply in through air intake passage 128 by opening valve flap 130 to fill the resuscitation bag. The diameters and tolerances of the various structures of this embodiment of the invention are governed by the considerations as in the previous embodiments, and therefore the same dimensions are acceptable. In this manner, exhalation gases are again prevented from contaminating the resuscitation bags as they are safely flowed through the exhalation passage 114.

While a particular embodiment of this invention is shown and described herein, it will be understood of course, that the invention is not to be limited thereto since many modifications may be made, particularly by those skilled in this art, in light of this disclosure. It is contemplated therefore by the appended claims to cover any such modifications as fall within the true spirit and scope of this invention.

What is claimed is:

1. A universal manual resuscitator valve, comprising:
    a valve body having a bore therethrough which defines a passage;
    an annular valve seat disposed in said bore;
    a valve element attached at one portion to said valve body in said bore and adjacent said valve seat such that said valve element seats on said valve seat in a first mode of operation,
    said valve element serving to partition said passage into a first portion and a second portion in said first mode of operation;
    an exhalation stem disposed in said valve body and defining an exhalation passage, said exhalation stem having a first end which projects into said bore at said first portion of said passage, said first end being beveled and positioned with respect to said valve element such that said valve element seats on said beveled end of said exhalation stem in a second mode of operation to close said exhalation passage;
    said valve body further having an inlet port disposed at said second portion of said passage;
    a one-way valve disposed on said valve body in said passage in association with said inlet port.

2. The universal manual resuscitator valve recited in claim 1, wherein said valve body is formed of transparent plastic.

3. The universal manual resuscitator valve recited in claim 1, wherein said valve body further includes a manometer pressure gauge port disposed at said first portion of said passage.

4. The universal manual resuscitator valve recited in claim 1, wherein said one-way valve in association with said inlet port includes a concave valve flap.

5. The universal manual resuscitator valve recited in claim 1, wherein said one-way valve in association with said inlet port includes a beveled valve seat.

6. The universal manual resuscitator valve recited in claim 1, wherein said valve element is a valve flap formed of a resilient material.

7. A valve assembly for use with a manual resuscitator bag and a patient face mask, said valve assembly comprising:
    a valve body defining an air passage;
    said valve body having a first end adapted to receive said bag and a second end adapted to receive said face mask;
    a valve seat attached to said valve body and extending at least partially into said air passage, said valve seat being adapted to receive a first valve flap;
    a first valve flap attached to one edge to a portion of said first valve seat and attached at an opposite edge to another portion of said first valve seat;
    said valve body further including an exhalation stack defining an exhalation passage in flow communication with said air passage in one mode of operation, one end of said exhalation stack being adjacent said first flap member a distance sufficient to allow said first flap member to substantially cover said end of said stack to block said exhalation passage in another mode of operation of said valve assembly; and
    said valve body further including an intake stack defining an intake passage having a second valve flap attached thereto for opening and closing said intake passage, said intake stack being positioned between said valve seat and said first end of said valve body.

8. The valve assembly recited in claim 7, wherein said second valve flap is at least partially concave.

9. The valve assembly recited in claim 7, wherein said second valve seat is beveled.

10. The valve assembly recited in claim 7, further including a viral/bacterial filter in association with said body at said first end adapted to substantially prevent viruses and bacteria from entering said bag.

* * * * *